United States Patent
Fisher et al.

(10) Patent No.: US 10,188,058 B2
(45) Date of Patent: Jan. 29, 2019

(54) SWEET CORN HYBRID SVSK6143 AND PARENTS THEREOF

(71) Applicant: Seminis Vegetable Seeds, Inc., St. Louis, MO (US)

(72) Inventors: David Elon Fisher, Waunakee, WI (US); Kendell B Hellewell, Nampa, ID (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 15/617,952

(22) Filed: Jun. 8, 2017

(65) Prior Publication Data

US 2018/0352769 A1     Dec. 13, 2018

(51) Int. Cl.
   *A01H 5/10*     (2018.01)
   *A01H 6/46*     (2018.01)

(52) U.S. Cl.
   CPC ............... *A01H 5/10* (2013.01); *A01H 6/46* (2018.05)

(58) Field of Classification Search
   None
   See application file for complete search history.

(56) References Cited

U.S. PATENT DOCUMENTS

| | | | |
|---|---|---|---|
| 7,157,625 B1 * | 1/2007 | Popi | A01H 5/10 435/412 |
| 8,062,840 B2 | 11/2011 | Anderson et al. | |
| 8,212,113 B2 | 7/2012 | Beazley et al. | |
| 8,502,025 B2 | 8/2013 | Fisher | |
| 8,575,462 B2 | 11/2013 | Fisher | |
| 8,581,078 B2 | 11/2013 | Hellewell et al. | |
| 8,766,062 B2 | 7/2014 | Fisher et al. | |
| 8,878,030 B2 | 11/2014 | Fisher et al. | |
| 9,029,658 B2 | 5/2015 | Fisher et al. | |
| 9,265,211 B2 | 2/2016 | Fisher et al. | |
| 9,277,693 B2 | 3/2016 | Fisher et al. | |
| 9,277,709 B2 | 3/2016 | Fisher et al. | |
| 9,277,710 B2 | 3/2016 | Fisher et al. | |
| 9,374,962 B2 | 6/2016 | Fisher et al. | |
| 9,491,918 B2 | 11/2016 | Fisher et al. | |
| 9,510,533 B2 | 12/2016 | Fisher et al. | |
| 2016/0165829 A1 | 6/2016 | Fisher et al. | |

OTHER PUBLICATIONS

U.S. Appl. No. 15/178,550, filed Jun. 9, 2016, Hellewell.
U.S. Appl. No. 15/178,552, filed Jun. 9, 2016, Hellewell.
U.S. Appl. No. 15/178,554, filed Jun. 9, 2016, Hellewell.
U.S. Appl. No. 15/178,555, filed Jun. 9, 2016, Hellewell.
U.S. Appl. No. 15/207,393, filed Jul. 11, 2016, Hellewell.
U.S. Appl. No. 15/618,091, filed Jun. 8, 2017, Fisher et al.
U.S. Appl. No. 15/618,093, filed Jun. 8, 2017, Hellewell.
U.S. Appl. No. 15/618,094, filed Jun. 8, 2017, Hellewell.
Hu et al., "Construction of 'compound' rust genes in maize," *Euphytica*, 87(1):45-51; 1996.
Larkin et al., "Somaclonal variation—a novel source of variability from cell cultures for plant improvement," *Theor Appl Genet*, 60(4):197-214; 1981.
Moose et al., "Molecular plant breeding as the foundation for 21st century crop improvement," *Plant Physiol*, 147(3):969-77, 2008.
Variety specific information as indicated in transmittal letter of Jun. 21, 2017 Information Disclosure Statement for U.S. Appl. No. 15/617,952.

* cited by examiner

*Primary Examiner* — Vinod Kumar
(74) *Attorney, Agent, or Firm* — Dentons US LLP; Alissa Eagle

(57) ABSTRACT

The invention provides seed and plants of corn hybrid SVSK6143 and the parent lines thereof. The invention thus relates to the plants, seeds, and tissue cultures of corn hybrid SVSK6143 and the parent lines thereof, and to methods for producing a corn plant produced by crossing such plants with themselves or with another corn plant, such as a plant of another genotype. The invention further relates to seeds and plants produced by such crossing. The invention further relates to parts of such plants, including the fruit and gametes of such plants.

22 Claims, No Drawings

SWEET CORN HYBRID SVSK6143 AND
PARENTS THEREOF

FIELD OF THE INVENTION

The present invention relates to the field of plant breeding and, more specifically, to the development of corn hybrid SVSK6143 and inbred corn lines SHY-6S15-9078LP and SHY-6RHBE322.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a corn plant of the hybrid designated SVSK6143, corn line SHY-6S15-9078LP, or corn line SHY-6RHBE322. Also provided are corn plants having all the physiological and morphological characteristics of such a plant. Parts of these corn plants are also provided, for example, including pollen, an ovule, scion, a rootstock, a fruit, and a cell of the plant.

In another aspect of the invention, a plant of corn hybrid SVSK6143 and/or corn lines SHY-6S15-9078LP and SHY-6RHBE322 comprising an added heritable trait is provided. The heritable trait may comprise a genetic locus that is, for example, a dominant or recessive allele. In one embodiment of the invention, a plant of corn hybrid SVSK6143 and/or corn lines SHY-6S15-9078LP and SHY-6RHBE322 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of corn hybrid SVSK6143 and/or corn lines SHY-6S15-9078LP and SHY-6RHBE322. The corn seed of the invention may be provided as an essentially homogeneous population of corn seed of corn hybrid SVSK6143 and/or corn lines SHY-6S15-9078LP and SHY-6RHBE322. Essentially homogeneous populations of seed are generally free from substantial numbers of other seed. Therefore, seed of hybrid SVSK6143 and/or corn lines SHY-6S15-9078LP and SHY-6RHBE322 may be defined as forming at least about 97% of the total seed, including at least about 98%, 99% or more of the seed. The seed population may be separately grown to provide an essentially homogeneous population of corn plants designated SVSK6143 and/or corn lines SHY-6S15-9078LP and SHY-6RHBE322.

In yet another aspect of the invention, a tissue culture of regenerable cells of a corn plant of hybrid SVSK6143 and/or corn lines SHY-6S15-9078LP and SHY-6RHBE322 is provided. The tissue culture will preferably be capable of regenerating corn plants capable of expressing all of the physiological and morphological characteristics of the starting plant and of regenerating plants having substantially the same genotype as the starting plant. Examples of some of the physiological and morphological characteristics of the hybrid SVSK6143 and/or corn lines SHY-6S15-9078LP and SHY-6RHBE322 include those traits set forth in the tables herein. The regenerable cells in such tissue cultures may be derived, for example, from embryos, meristems, cotyledons, pollen, leaves, anthers, roots, root tips, pistils, flowers, seeds, stalks, silks, tassels, kernels, ears, cobs, and husks. Still further, the present invention provides corn plants regenerated from a tissue culture of the invention, the plants having all the physiological and morphological characteristics of hybrid SVSK6143 and/or corn lines SHY-6515-9078LP and SHY-6RHBE322.

In still yet another aspect of the invention, processes are provided for producing corn seeds, plants, and fruit, which processes generally comprise crossing a first parent corn plant with a second parent corn plant, wherein at least one of the first or second parent corn plants is a plant of corn line SHY-6S15-9078LP or corn line SHY-6RHBE322. These processes may be further exemplified as processes for preparing hybrid corn seed or plants, wherein a first corn plant is crossed with a second corn plant of a different, distinct genotype to provide a hybrid that has, as one of its parents, a plant of corn line SHY-6S15-9078LP or corn line SHY-6RHBE322. In these processes, crossing will result in the production of seed. The seed production occurs regardless of whether the seed is collected or not.

In one embodiment of the invention, the first step in "crossing" comprises planting seeds of a first and second parent corn plant, often in proximity so that pollination will occur for example, mediated by insect vectors. Alternatively, pollen can be transferred manually. Where the plant is self-pollinated, pollination may occur without the need for direct human intervention other than plant cultivation. For hybrid crosses, it may be beneficial to detassel or otherwise emasculate the parent used as a female.

A second step may comprise cultivating or growing the seeds of first and second parent corn plants into mature plants. A third step may comprise preventing self-pollination of the plants, such as by detasseling or other means.

A fourth step for a hybrid cross may comprise cross-pollination between the first and second parent corn plants. Yet another step comprises harvesting the seeds from at least one of the parent corn plants. The harvested seed can be grown to produce a corn plant or hybrid corn plant.

The present invention also provides the corn seeds and plants produced by a process that comprises crossing a first parent corn plant with a second parent corn plant, wherein at least one of the first or second parent corn plants is a plant of corn hybrid SVSK6143 and/or corn lines SHY-6S15-9078LP and SHY-6RHBE322. In one embodiment of the invention, corn seed and plants produced by the process are first generation ($F_1$) hybrid corn seed and plants produced by crossing a plant in accordance with the invention with another, distinct plant. The present invention further contemplates plant parts of such an $F_1$ hybrid corn plant and methods of use thereof. Therefore, certain exemplary embodiments of the invention provide an $F_1$ hybrid corn plant and seed thereof.

In still yet another aspect, the present invention provides a method of producing a plant derived from hybrid SVSK6143 and/or corn lines SHY-6S15-9078LP and SHY-6RHBE322, the method comprising the steps of: (a) preparing a progeny plant derived from hybrid SVSK6143 and/or corn lines SHY-6S15-9078LP and SHY-6RHBE322, wherein said preparing comprises crossing a plant of the hybrid SVSK6143 and/or corn lines SHY-6S15-9078LP and SHY-6RHBE322 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid SVSK6143 and/or corn lines SHY-6S15-9078LP and SHY-6RHBE322. The plant derived from hybrid SVSK6143 and/or corn lines SHY-6S15-9078LP and SHY-6RHBE322 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid SVSK6143 and/or corn lines SHY-6S15-9078LP and SHY-6RHBE322 is obtained which possesses some of the desirable traits of the line/hybrid as well as potentially other selected traits.

In certain embodiments, the present invention provides a method of producing food or feed comprising: (a) obtaining a plant of corn hybrid SVSK6143 and/or corn lines SHY-6S15-9078LP and SHY-6RHBE322, wherein the plant has been cultivated to maturity, and (b) collecting at least one corn from the plant.

In still yet another aspect of the invention, the genetic complement of corn hybrid SVSK6143 and/or corn lines SHY-6S15-9078LP and SHY-6RHBE322 is provided. The phrase "genetic complement" is used to refer to the aggregate of nucleotide sequences, the expression of which sequences defines the phenotype of, in the present case, a corn plant, or a cell or tissue of that plant. A genetic complement thus represents the genetic makeup of a cell, tissue, or plant, and a hybrid genetic complement represents the genetic make-up of a hybrid cell, tissue, or plant. The invention thus provides corn plant cells that have a genetic complement in accordance with the corn plant cells disclosed herein and seeds and plants containing such cells.

Plant genetic complements may be assessed by genetic marker profiles and by the expression of phenotypic traits that are characteristic of the expression of the genetic complement, e.g., isozyme typing profiles. It is understood that hybrid SVSK6143 and/or corn lines SHY-6S15-9078LP and SHY-6RHBE322 could be identified by any of the many well-known techniques such as, for example, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In still yet another aspect, the present invention provides hybrid genetic complements, as represented by corn plant cells, tissues, plants, and seeds, formed by the combination of a haploid genetic complement of a corn plant of the invention with a haploid genetic complement of a second corn plant, preferably, another, distinct corn plant. In another aspect, the present invention provides a corn plant regenerated from a tissue culture that comprises a hybrid genetic complement of this invention.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features, and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds, and derivatives of corn hybrid SVSK6143, corn line SHY-6515-9078LP, and corn line SHY-6RHBE322.

Corn hybrid SVSK6143, also known as 15-6S-SHY-6143, is a yellow sh2 variety intended for the processing market that comprises the RpG5 gene conferring resistance to common rust.

Corn line SHY-6S15-9078LP is a yellow sh2 inbred variety that comprises the Ht1 gene conferring resistance to select races of Northern corn leaf blight.

Corn line SHY-6RHBE322 is an inbred variety that comprises the RpG5 gene conferring resistance to common rust.

A. Origin and Breeding History of Corn Hybrid SVSK6143

The parents of hybrid SVSK6143 are SHY-6515-9078LP and SHY-6RHBE322. The parent lines are uniform and stable, as is a hybrid produced therefrom. A small percentage of variants can occur within commercially acceptable limits for almost any characteristic during the course of repeated multiplication. However no variants are expected.

B. Physiological and Morphological Characteristics of Corn Hybrid SVSK6143, Corn Line SHY-6S15-9078LP, and Corn Line SHY-6RHBE322

In accordance with one aspect of the present invention, there is provided a plant having the physiological and morphological characteristics of corn hybrid SVSK6143 and the parent lines thereof. A description of the physiological and morphological characteristics of such plants is presented in Tables 1-3.

TABLE 1

Physiological and Morphological Characteristics of Corn Hybrid SVSK6143

| | CHARACTERISTIC | SVSK6143 | BASIN R |
|---|---|---|---|
| 1. | Type | sweet | sweet |
| 2. | Maturity in the Region of Best Adaptability | | |
| | emergence to 50% of plants in silk | 57 days 2191.7 heat units | 54 days 2070.2 heat units |
| | emergence to 50% of plants in pollen | 56 days 2153.5 heat units | 52 days 1989.6 heat units |
| | 10% to 90% pollen shed | 4 days 200.5 heat units | 4 days 189.9 heat units |
| | 50% silk to optimum edible quality | 27 days 1122.4 heat units | 27 days 1375.1 heat units |
| 3. | Plant | | |
| | length (tassel included) | medium | medium |
| | plant height (to tassel tip) (cm) | avg: 163.06 std dev: 26.9191 sample size: 15 | avg: 176.86 std dev: 13.6008 sample size: 15 |
| | ear height (to base of top ear node) (cm) | avg: 55.53 std dev: 6.7493 sample size: 15 | avg: 51.06 std dev: 7.6855 sample size: 15 |
| | length of top ear internode (cm) | avg: 14.5 std dev: 1.0351 sample size: 15 | avg: 14.63 std dev: 0.7898 sample size: 15 |
| | average number of tillers | avg: 2.46 std dev: 0.8338 sample size: 15 | avg: 2.66 std dev: 1.0465 sample size: 15 |
| | average number of ears per stalk | avg: 1.66 std dev: 0.50709 sample size: 15 | avg: 1.93 std dev: 0.5936 sample size: 15 |
| | anthocyanin of brace roots | absent | absent |
| | stem, degree of zig-zag | absent or very slight | absent or very slight |
| | stem, anthocyanin coloration of internodes | absent or very weak | absent or very weak |
| | ratio height of insertion of | medium | medium |

TABLE 1-continued

Physiological and Morphological Characteristics of Corn Hybrid SVSK6143

| | CHARACTERISTIC | SVSK6143 | BASIN R |
|---|---|---|---|
| | peduncle of upper ear to plant length | | |
| 4. | Leaf | | |
| | shape of apex | pointed | rounded |
| | undulation of margin of blade | intermediate | intermediate |
| | width of blade | wide | wide |
| | curvature of blade | slightly recurved | moderately recurved |
| | width of ear node leaf (cm) | avg: 8.93 std dev: 0.4577 sample size: 15 | avg: 9.58 std dev: 0.7532 sample size: 15 |
| | length of ear node leaf (cm) | avg: 77.2 std dev: 3.5143 sample size: 15 | avg: 77.4 std dev: 3.8601 sample size: 15 |
| | number of leaves above top ear | avg: 5.73 std dev: 0.5936 sample size: 15 | avg: 6.06 std dev: 0.7988 sample size: 15 |
| | degrees leaf angle (second leaf above ear at anthesis to stalk above leaf) | 40° | 55° |
| | angle between blade and stem (leaf just above upper ear) | small (±25°) | medium (±50°) |
| | color (Munsell color chart code) | 5GY 4/4 | 5GY 3/4 |
| | intensity of green color | dark | dark |
| | sheath pubescence (scale from 1 (none) to 9 (like peach fuzz)) | 9 | 8 |
| | marginal waves (scale from 1 (none) to 9 (many)) | 7 | 8 |
| | longitudinal creases (scale from 1 (none) to 9 (many)) | 3 | 4 |
| | anthocyanin coloration of sheath (first leaf) | absent or very weak | absent or very weak |
| | anthocyanin coloration of sheath (middle of plant) | absent or very weak | absent or very weak |
| | peduncle length | medium | very long |
| 5. | Tassel | | |
| | number of primary lateral branches | avg: 30.9 std dev: 3.9364 sample size: 15 | avg: 20.13 std dev: 3.889 sample size: 15 |
| | branch angle from central spike | avg: 24° std dev: 16.3881° sample size: 15 | avg: 55.7° std dev: 9.037° sample size: 15 |
| | tassel length (top leaf collar to tassel tip) (cm) | avg: 38.46 std dev: 1.302 sample size: 15 | avg: 37.86 std dev: 2.612 sample size: 15 |
| | density of spikeletes | moderately dense | moderately dense |
| | pollen shed (scale from 0 (male sterile) to 9 (heavy shed)) | 3 | 8 |
| | anther color (Munsell color chart code) | 2.5GY 7/6 | 2.5GY 7/6 |
| | anthocyanin coloration of anthers (middle third of main axis) | absent or very weak | absent or very weak |
| | glume color (Munsell color chart code) | 2.5GY 8/6 | 5GY 6/8 |
| | bar glumes (glume bands) | absent | absent |
| | anthocyanin coloration at base of glume (middle third of main axis) | absent or very weak | absent or very weak |
| | anthocyanin coloration of glume (excluding base) | absent or very weak | absent or very weak |
| | time of anthesis (middle third of main axis, 50% of plants) | very early to early | early to medium |
| | angle between main axis and lateral branches (lower third of tassel) | small (±25°) | medium (±50°) |
| | curvature of lateral branches (lower third of tassel) | absent or very slightly recurved | moderately recurved |
| | number of primary lateral branches | many | medium |
| | length of main axis above lowest lateral branch | long | very long |

TABLE 1-continued

Physiological and Morphological Characteristics of Corn Hybrid SVSK6143

| | CHARACTERISTIC | SVSK6143 | BASIN R |
|---|---|---|---|
| | length of main axis above highest lateral branch | short | short |
| | length of lateral branch | medium | medium |
| 6. | Ear | | |
| | length | very long | very long |
| | diameter (middle) | large | large |
| | shape | conico-cylindrical | cylindrical |
| | time of silk emergence (50% of plants) | early | early |
| | anthocyanin coloration of silks | absent or very weak | absent or very weak |
| | silk color (unhusked) (Munsell color chart code) (3 days after emergence) | 2.5GY 8/4 | 2.5GY 8/6 |
| | fresh husk color (unhusked) (Munsell color chart code) (25 days after 50% silking) | 5GY 7/6 | 2.5GY 7/6 |
| | husk tightness (unhusked) (scale from 1 (very loose) to 9 (very tight)) | 8 | 6 |
| | husk extension (unhusked) (at harvest) | short (ears exposed) | short (ears exposed) |
| | ear length (husked) (cm) | avg: 21.85 std dev: 0.6236 sample size: 15 | avg: 24.75 std dev: 0.8271 sample size: 15 |
| | ear diameter at mid-point (husked) (mm) | avg: 50.71 std dev: 4.0254 sample size: 15 | avg: 50 std dev: 1.727 sample size: 15 |
| | ear weight (husked) (g) | avg: 345.53 std dev: 3.0675 sample size: 15 | avg: 369.46 std dev: 41.026 sample size: 15 |
| | number of kernel rows (husked) | avg: 20.93 std dev: 1.5796 sample size: 15 | avg: 16.6 std dev: 1.298 sample size: 15 |
| | kernel rows (husked) | distinct | distinct |
| | row alignment (husked) | straight | straight |
| | shank length (husked) (cm) | avg: 14.32 std dev: 2.1452 sample size: 15 | avg: 17.9 std dev: 4.918 sample size: 15 |
| | ear taper (husked) | slight | slight |
| | number of rows of grain | many | many |
| | number of colors of grains | two | one |
| | grain, intensity of yellow color | light | dark |
| | grain length | medium | medium |
| | grain width | narrow | narrow |
| | type of grain | sweet | sweet |
| | shrinkage of top of grain | medium | medium |
| | color of top of grain | yellow | yellow orange |
| 7. | Cob | | |
| | anthocyanin coloration of glumes of cob | absent or very weak | absent or very weak |
| | cob diameter at mid-point (mm) | avg: 32.45 std dev: 2.6109 sample size: 15 | avg: 31.50 std dev: 2.256 sample size: 15 |
| | cob color (Munsell color chart code) | 158A | 161D |

*These are typical values. Values may vary due to environment. Other values that are substantially equivalent are within the scope of the invention.

TABLE 2

Physiological and Morphological Characteristics of Corn Line SHY-6S15-9078LP

| | CHARACTERISTIC | SHY-6S15-9078LP | FA 32 |
|---|---|---|---|
| 1. | Type | sweet | sweet |
| 2. | Maturity in the Region of Best Adaptability | | |
| | emergence to 50% of plants | 63 days | 63 days |
| | in silk | 2418.7 heat units | 2500.1 heat units |
| | emergence to 50% of plants in pollen | 61 days 2338.6 heat units | 59 days 2326 heat units |
| | 10% to 90% pollen shed | 5 days 227.1 heat units | 4 days 214.6 heat units |
| | 50% silk to optimum edible quality | 24 days 1025 heat units | 21 days 890.6 heat units |
| 3. | Plant | | |
| | length (tassel included) | short | short |
| | plant height (to tassel tip) (cm) | avg: 113.53 std dev: 18.724 sample size: 15 | avg: 145.86 std dev: 5.777 sample size: 15 |
| | ear height (to base of top ear node) (cm) | avg: 19.5 std dev: 8.2959 sample size: 15 | avg: 46.3 std dev: 8.1871 sample size: 15 |
| | length of top ear internode (cm) | avg: 7.5 std dev: 1.6611 sample size: 15 | avg: 12 std dev: 0.8259 sample size: 15 |
| | average number of tillers | avg: 2.5 std dev: 1.187 sample size: 15 | avg: 3 std dev: 1.2536 sample size: 15 |
| | average number of ears per stalk | avg: 1.86 std dev: 0.5164 sample size: 15 | avg: 2 std dev: 0 sample size: 15 |
| | anthocyanin of brace roots | absent | absent |
| | stem, degree of zig-zag | absent or very slight | slight |
| | stem, anthocyanin coloration of internodes | absent or very weak | absent or very weak |
| | ratio height of insertion of peduncle of upper ear to plant length | small | medium |
| 4. | Leaf | | |
| | shape of apex | pointed | pointed |
| | undulation of margin of blade | intermediate | intermediate |
| | width of blade | medium | medium |
| | curvature of blade | slightly recurved | slightly recurved |
| | width of ear node leaf (cm) | avg: 9.0 std dev: 0.7326 sample size: 15 | avg: 7.36 std dev: 0.3498 sample size: 15 |
| | length of ear node leaf (cm) | avg: 57.6 std dev: 7.7917 sample size: 15 | avg: 69.76 std dev: 2.3058 sample size: 15 |
| | number of leaves above top ear | avg: 6.4 std dev: 1.5056 sample size: 15 | avg: 4.66 std dev: 0.7238 sample size: 15 |
| | degrees leaf angle (second leaf above ear at anthesis to stalk above leaf) | 30° | 37° |
| | angle between blade and stem (leaf just above upper ear) | small (±25°) | small (±25°) |
| | color (Munsell color chart code) | 7.5GY 3/4 | 5GY 3/4 |
| | intensity of green color | dark | medium |
| | sheath pubescence (scale from 1 (none) to 9 (like peach fuzz)) | 4 | 7 |
| | marginal waves (scale from 1 (none) to 9 (many)) | 6 | 7 |
| | longitudinal creases (scale from 1 (none) to 9 (many)) | 7 | 6 |
| | anthocyanin coloration of sheath (first leaf) | absent or very weak | absent or very weak |
| | anthocyanin coloration of sheath (middle of plant) | absent or very weak | absent or very weak |
| | peduncle length | medium | medium |
| 5. | Tassel | | |
| | number of primary lateral branches | avg: 31.8 std dev: 7.771 sample size: 15 | avg: 15.4 std dev: 4.0673 sample size: 15 |
| | branch angle from central spike | avg: 53.93° std dev: 13.3602° sample size: 15 | avg: 67° std dev: 13.2406° sample size: 15 |
| | tassel length (top leaf collar | avg: 30.3 | avg: 38.22 |

TABLE 2-continued

Physiological and Morphological Characteristics of Corn Line SHY-6S15-9078LP

| | CHARACTERISTIC | SHY-6S15-9078LP | FA 32 |
|---|---|---|---|
| | to tassel tip) (cm) | std dev: 3.4527 sample size: 15 | std dev: 2.3098 sample size: 15 |
| | density of spikeletes | moderately dense | medium |
| | pollen shed (scale from 0 (male sterile) to 9 (heavy shed)) | 8 | 7 |
| | anther color (Munsell color chart code) | 2.5GY 7/4 | 2.5GY 8/8 |
| | anthocyanin coloration of anthers (middle third of main axis) | absent or very weak | absent or very weak |
| | glume color (Munsell color chart code) | 5GY 5/2 | 5GY 6/4 |
| | bar glumes (glume bands) | absent | absent |
| | anthocyanin coloration at base of glume (middle third of main axis) | absent or very weak | absent or very weak |
| | anthocyanin coloration of glume (excluding base) | absent or very weak | absent or very weak |
| | time of anthesis (middle third of main axis, 50% of plants) | late | late |
| | angle between main axis and lateral branches (lower third of tassel) | small (±25°) | large (±75°) |
| | curvature of lateral branches (lower third of tassel) | slightly recurved | strongly recurved |
| | number of primary lateral branches | many | medium |
| | length of main axis above lowest lateral branch | long | medium |
| | length of main axis above highest lateral branch | short | short |
| | length of lateral branch | short | very long |
| 6. | Ear | | |
| | length | medium | medium |
| | diameter (middle) | medium | medium |
| | shape | cylindrical | cylindrical |
| | time of silk emergence (50% of plants) | early | early |
| | anthocyanin coloration of silks | absent or very weak | absent or very weak |
| | silk color (unhusked) (Munsell color chart code) (3 days after emergence) | 2.5GY 8/4 | 2.5GY 8/6 |
| | fresh husk color (unhusked) (Munsell color chart code) (25 days after 50% silking) | 5GY 6/6 | 2.5GY 8/6 |
| | husk tightness (unhusked) (scale from 1 (very loose) to 9 (very tight)) | 8 | 8 |
| | husk extension (unhusked) (at harvest) | medium (<8 cm) | medium (<8 cm) |
| | ear length (husked) (cm) | avg: 18.7 std dev: 2.5128 sample size: 15 | avg: 17.36 std dev: 2.1336 sample size: 15 |
| | ear diameter at mid-point (husked) (mm) | avg: 33.44 std dev: 8.709 sample size: 15 | avg: 43.86 std dev: 3.2361 sample size: 15 |
| | ear weight (husked) (g) | avg: 172.26 std dev: 32.605 sample size: 15 | avg: 153 std dev: 39.77 sample size: 15 |
| | number of kernel rows (husked) | avg: 18.86 std dev: 1.407 sample size: 15 | avg: 15.73 std dev: 1.9809 sample size: 15 |
| | kernel rows (husked) | distinct | indistinct |
| | row alignment (husked) | slightly curved | slightly curved |
| | shank length (husked) (cm) | avg: 15.86 std dev: 3.6188 sample size: 15 | avg: 17.9 std dev: 4.9034 sample size: 15 |
| | ear taper (husked) | average | slight |
| | number of rows of grain | medium | medium |
| | number of colors of grains | one | one |
| | grain, intensity of yellow color | light | medium |
| | grain length | medium | medium |
| | grain width | medium | narrow |
| | type of grain | sweet | sweet |
| | shrinkage of top of grain | weak | medium |
| | color of top of grain | yellowish white | yellow |
| 7. | Cob | | |
| | anthocyanin coloration of glumes of cob | absent or very weak | absent or very weak |
| | cob diameter at mid-point (mm) | avg: 34.30 std dev: 2.3113 sample size: 15 | avg: 32.08 std dev: 2.9177 sample size: 15 |
| | cob color (Munsell color chart code) | 160C | 13B |

*These are typical values. Values may vary due to environment. Other values that are substantially equivalent are within the scope of the invention.

TABLE 3

Physiological and Morphological Characteristics of Corn Line SHY-6RHBE322

| | CHARACTERISTIC | SHY-6RHBE322 | FA 32 |
|---|---|---|---|
| 1. | Type | sweet | sweet |
| 2. | Maturity in the Region of Best Adaptability | | |
| | emergence to 50% of plants in silk | 68 days 2609.1 heat units | 63 days 2500.1 heat units |
| | emergence to 50% of plants in pollen | 61 days 2310.75 heat units | 59 days 2326 heat units |
| | 10% to 90% pollen shed | 5 days 190.55 heat units | 4 days 214.6 heat units |
| | 50% silk to optimum edible quality | 23 days 934.75 heat units | 21 days 890.6 heat units |
| 3. | Plant | | |
| | length (tassel included) | medium | short |
| | plant height (to tassel tip) (cm) | avg: 178.23 std dev: 12.0532 sample size: 15 | avg: 145.86 std dev: 5.777 sample size: 15 |
| | ear height (to base of top ear node) (cm) | avg: 57.9 std dev: 12.6267 sample size: 15 | avg: 46.3 std dev: 8.1871 sample size: 15 |
| | length of top ear internode (cm) | avg: 14.34 std dev: 1.0308 sample size: 15 | avg: 12 std dev: 0.8259 sample size: 15 |
| | average number of tillers | avg: 1.4 std dev: 1.0555 sample size: 15 | avg: 3 std dev: 1.2536 sample size: 15 |
| | average number of ears per stalk | avg: 1.6 std dev: 0.6324 sample size: 15 | avg: 2 std dev: 0 sample size: 15 |
| | anthocyanin of brace roots | absent | absent |
| | stem, degree of zig-zag | absent or very slight | slight |
| | stem, anthocyanin coloration of internodes | absent or very weak | absent or very weak |
| | ratio height of insertion of peduncle of upper ear to plant length | medium | medium |
| 4. | Leaf | | |
| | shape of apex | pointed | pointed |
| | undulation of margin of blade | intermediate | intermediate |
| | width of blade | medium | medium |
| | curvature of blade | slightly recurved | slightly recurved |
| | width of ear node leaf (cm) | avg: 7.96 std dev: 0.5207 sample size: 15 | avg: 7.36 std dev: 0.3498 sample size: 15 |
| | length of ear node leaf (cm) | avg: 73.35 std dev: 4.5998 sample size: 15 | avg: 69.76 std dev: 2.3058 sample size: 15 |

TABLE 3-continued

Physiological and Morphological Characteristics of Corn Line SHY-6RHBE322

| CHARACTERISTIC | SHY-6RHBE322 | FA 32 |
|---|---|---|
| number of leaves above top ear | avg: 5.33 std dev: 0.6172 sample size: 15 | avg: 4.66 std dev: 0.7238 sample size: 15 |
| degrees leaf angle (second leaf above ear at anthesis to stalk above leaf) | 42° | 37° |
| angle between blade and stem (leaf just above upper ear) | small (±25°) | small (±25°) |
| color (Munsell color chart code) | 5GY 3/4 | 5GY 3/4 |
| intensity of green color | medium | medium |
| sheath pubescence (scale from 1 (none) to 9 (like peach fuzz)) | 4 | 7 |
| marginal waves (scale from 1 (none) to 9 (many)) | 6 | 7 |
| longitudinal creases (scale from 1 (none) to 9 (many)) | 5 | 6 |
| anthocyanin coloration of sheath (first leaf) | absent or very weak | absent or very weak |
| anthocyanin coloration of sheath (middle of plant) | absent or very weak | absent or very weak |
| peduncle length | medium | medium |
| 5. Tassel | | |
| number of primary lateral branches | avg: 22.66 std dev: 7.4322 sample size: 15 | avg: 15.4 std dev: 4.0673 sample size: 15 |
| branch angle from central spike | avg: 40.2° std dev: 7.5517° sample size: 15 | avg: 67° std dev: 13.2406° sample size: 15 |
| tassel length (top leaf collar to tassel tip) (cm) | avg: 30.46 std dev: 2.665 sample size: 15 | avg: 38.22 std dev: 2.3098 sample size: 15 |
| density of spikeletes | medium | medium |
| pollen shed (scale from 0 (male sterile) to 9 (heavy shed)) | 7 | 7 |
| anther color (Munsell color chart code) | 2.5GY 8/10 | 2.5GY 8/8 |
| anthocyanin coloration of anthers (middle third of main axis) | absent or very weak | absent or very weak |
| glume color (Munsell color chart code) | 2.5GY 6/4 | 5GY 6/4 |
| bar glumes (glume bands) | absent | absent |
| anthocyanin coloration at base of glume (middle third of main axis) | absent or very weak | absent or very weak |
| anthocyanin coloration of glume (excluding base) | absent or very weak | absent or very weak |
| time of anthesis (middle third of main axis, 50% of plants) | late | late |
| angle between main axis and lateral branches (lower third of tassel) | medium (±50°) | large (±75°) |
| curvature of lateral branches (lower third of tassel) | moderately recurved | strongly recurved |
| number of primary lateral branches | medium | medium |
| length of main axis above lowest lateral branch | very long | medium |
| length of main axis above highest lateral branch | long | short |
| length of lateral branch | short | very long |
| 6. Ear | | |
| length | medium | medium |
| diameter (middle) | medium | medium |
| shape | cylindrical | cylindrical |
| time of silk emergence (50% of plants) | early to medium | early |
| anthocyanin coloration of silks | absent or very weak | absent or very weak |
| silk color (unhusked) (Munsell color chart code) (3 days after emergence) | 2.5GY 8/4 | 2.5GY 8/6 |
| fresh husk color (unhusked) (Munsell color chart code) (25 days after 50% silking) | 5GY 7/6 | 2.5GY 8/6 |
| husk tightness (unhusked) (scale from 1 (very loose) to 9 (very tight)) | 8 | 8 |
| husk extension (unhusked) (at harvest) | medium (<8 cm) | medium (<8 cm) |
| ear length (husked) (cm) | avg: 18.73 std dev: 0.8632 sample size: 15 | avg: 17.36 std dev: 2.1336 sample size: 15 |
| ear diameter at mid-point (husked) (mm) | avg: 43.18 std dev: 2.3075 sample size: 15 | avg: 43.86 std dev: 3.2361 sample size: 15 |
| ear weight (husked) (g) | avg: 156.8 std dev: 34.2604 sample size: 15 | avg: 153 std dev: 39.77 sample size: 15 |
| number of kernel rows (husked) | avg: 18.4 std dev: 1.7237 sample size: 15 | avg: 15.73 std dev: 1.9809 sample size: 15 |
| kernel rows (husked) | indistinct | indistinct |
| row alignment (husked) | slightly curved | slightly curved |
| shank length (husked) (cm) | avg: 14.8 std dev: 3.0434 sample size: 15 | avg: 17.9 std dev: 4.9034 sample size: 15 |
| ear taper (husked) | average | slight |
| number of rows of grain | medium | medium |
| number of colors of grains | two | one |
| grain, intensity of yellow color | medium | medium |
| grain length | medium | medium |
| grain width | medium | narrow |
| type of grain | sweet | sweet |
| shrinkage of top of grain | strong | medium |
| color of top of grain | yellow | yellow |
| 7. Cob | | |
| anthocyanin coloration of glumes of cob | absent or very weak | absent or very weak |
| cob diameter at mid-point (mm) | avg: 31.78 std dev: 2.8231 sample size: 15 | avg: 32.08 std dev: 2.9177 sample size: 15 |
| cob color (Munsell color chart code) | 158A | 13B |

*These are typical values. Values may vary due to environment. Other values that are substantially equivalent are within the scope of the invention.

C. Breeding Corn Plants

One aspect of the current invention concerns methods for producing seed of corn hybrid SVSK6143 involving crossing corn lines SHY-6S15-9078LP and SHY-6RHBE322. Alternatively, in other embodiments of the invention, hybrid SVSK6143, line SHY-6S15-9078LP, or line SHY-6RHBE322 may be crossed with itself or with any second plant. Such methods can be used for propagation of hybrid SVSK6143 and/or the corn lines SHY-6S15-9078LP and SHY-6RHBE322 or can be used to produce plants that are derived from hybrid SVSK6143 and/or the corn lines SHY-6515-9078LP and SHY-6RHBE322. Plants derived from hybrid SVSK6143 and/or the corn lines SHY-6515-9078LP and SHY-6RHBE322 may be used, in certain embodiments, for the development of new corn varieties.

The development of new varieties using one or more starting varieties is well known in the art. In accordance with the invention, novel varieties may be created by crossing a plant of the invention followed by multiple generations of breeding according to such well-known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid induction systems have been developed for various plants to produce haploid tissues, plants and seeds. The haploid induction system can produce haploid plants from any genotype by crossing with an inducer line. Inducer lines and methods for obtaining haploid plants are known in the art.

Haploid embryos may be produced, for example, from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with SVSK6143 and/or corn lines SHY-6S15-9078LP and SHY-6RHBE322 for the purpose of developing novel corn lines, it will typically be preferred to choose those plants which either themselves exhibit one or more selected desirable characteristics or which exhibit the desired characteristic(s) when in hybrid combination. Examples of desirable traits may include, in specific embodiments, male sterility, herbicide resistance, resistance for bacterial, fungal, or viral disease, insect resistance, male fertility, sugar content, and enhanced nutritional quality.

D. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those corn plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental corn plant which contributes the locus for the desired characteristic is termed the nonrecurrent or donor parent. This terminology refers to the fact that the nonrecurrent parent is used one time in the backcross protocol and therefore does not recur. The parental corn plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a corn plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny corn plants of a backcross in which a plant described herein is the recurrent parent comprise (i) the desired trait from the non-recurrent parent and (ii) all of the physiological and morphological characteristics of corn the recurrent parent as determined at the 5% significance level when grown in the same environmental conditions.

New varieties can also be developed from more than two parents. The technique, known as modified backcrossing, uses different recurrent parents during the backcrossing.

Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiol.*, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, waxy starch, herbicide resistance, resistance to bacterial, fungal, or viral disease, insect resistance, sugar content, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of corn plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

E. Plants Derived by Genetic Engineering

Many useful traits that can be introduced by backcrossing, as well as directly into a plant, are those which are introduced by molecular genetic methods. Such methods include, but are not limited to, various plant transformation techniques and methods for site-specific recombination, the use of which are well-known in the art, and include, for example, the CRISPR-Cas system, zinc-finger nucleases (ZFNs), and transcription activator-like effector nucleases (TALENs), among others.

In one embodiment of the invention, genetic transformation may be used to insert a selected transgene into a plant of the invention or may, alternatively, be used for the preparation of transgenes which can be introduced by backcrossing. Methods for the transformation of plants that are well-known to those of skill in the art and applicable to many crop species include, but are not limited to, electroporation, microprojectile bombardment, *Agrobacterium*-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and, preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Nat. Biotechnol.*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13:344-348, 1994) and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S); the nopaline synthase promoter (An et al., *Plant Physiol.*, 88:547, 1988); the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wunl, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a corn plant according to the invention. Non-limiting examples of particular genes and corresponding phenotypes one may choose to introduce into a corn plant include one or more genes for insect tolerance, such as a *Bacillus thuringiensis* (B.t.) gene, pest tolerance such as genes for fungal disease control, herbicide tolerance such as genes conferring glyphosate tolerance and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

F. Male Sterility

Examples of genes conferring male sterility include those disclosed in U.S. Pat. Nos. 3,861,709, 3,710,511, 4,654,465, 5,625,132, and 4,727,219, each of the disclosures of which are specifically incorporated herein by reference in their entirety. Male sterility genes can increase the efficiency with which hybrids are made, in that they eliminate the need to physically emasculate the corn plant used as a female in a given cross.

Where one desires to employ male-sterility systems with a corn plant in accordance with the invention, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the corn plant is utilized, e.g., for silage, but in most cases, the seeds will be deemed the most valuable portion of the crop, so fertility of the hybrids in these crops must be restored. Therefore, one aspect of the current invention concerns a corn plant of the invention comprising a genetic locus capable of restoring male fertility in an otherwise male-sterile plant. Examples of male-sterility genes and corresponding restorers which could be employed with the plants of the invention are well known to those of skill in the art of plant breeding and are disclosed in, for instance, U.S. Pat. Nos. 5,530,191; 5,689,041; 5,741,684; and 5,684,242, the disclosures of which are each specifically incorporated herein by reference in their entirety.

G. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., *EMBO J.*, 7:1241, 1988; Gleen et al., *Plant Molec. Biology*, 18:1185-1187, 1992; and Miki et al., *Theor. Appl. Genet.*, 80:449, 1990.

Resistance genes for glyphosate (resistance conferred by mutant 5-enolpyruvylshikimate-3-phosphate synthase (EPSPS) and aroA genes, respectively), and hygromycin B phosphotransferase, and to other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. A hygromycin B phosphotransferase gene from *E. coli* that confers resistance to glyphosate in tobacco callus and plants is described in Penaloza-Vazquez et al. (*Plant Cell Reports*, 14:482-487, 1995). European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al. DeGreef et al., (*Biotechnology*, 7:61, 1989), describe the production of transgenic plants that express chimeric bar genes coding for phosphinothricin acetyl transferase activity. Exemplary of genes conferring resistance to phenoxy propionic acids and cyclohexanediones, such as sethoxydim and haloxyfop are the Acct-S1, Accl-S2 and Acct-S3 genes described by Marshall et al., (*Theor. Appl. Genet.*, 83:4:35, 1992).

Genes conferring resistance to a herbicide that inhibits photosynthesis are also known, such as a triazine (psbA and gs+ genes) and a benzonitrile (nitrilase gene). Przibilla et al., (*Plant Cell*, 3:169, 1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., (*Biochem. J.*, 285(Pt 1):173-180, 1992). Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS*, 103(33):12329-2334, 2006). The herbicide methyl viologen inhibits $CO_2$ assimilation. Foyer et al. (*Plant Physiol.*, 109:1047-1057, 1995) describe a plant overexpressing glutathione reductase (GR) which is resistant to methyl viologen treatment.

Siminszky (*Phytochemistry Reviews*, 5:445-458, 2006) describes plant cytochrome P450-mediated detoxification of multiple, chemically unrelated classes of herbicides.

H. Waxy Starch

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits additional progeny testing, for example growing additional generations such as the BC1S1, may be required to determine which plants carry the recessive gene.

I. Disease Resistance

Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones et al., *Science*, 266:7891, 1994 (cloning of the tomato Cf-9 gene for resistance to *Cladosporium flavum*); Martin et al., *Science*, 262: 1432, 1993 (tomato Pto gene for resistance to *Pseudomonas syringae* pv.); and Mindrinos et al., *Cell*, 78(6):1089-1099, 1994 (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (*Ann. Rev. Phytopathol.*, 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al., (*Nature*, 366:469, 1993), who show that transgenic plants expressing recombinant antibody genes are protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., *Plant Cell*, 8:1809-1819, 1996).

Logemann et al., (*Biotechnology*, 10:305, 1992), for example, disclose transgenic plants expressing a barley ribosome-inactivating gene have an increased resistance to fungal disease. Plant defensins may be used to provide resistance to fungal pathogens (Thomma et al., *Planta*, 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; 6,316,407; and 6,506,962.

J. Insect Resistance

One example of an insect resistance gene includes a *Bacillus thuringiensis* (Bt) protein, a derivative thereof or a synthetic polypeptide modeled thereon. See, for example, Geiser et al., (*Gene*, 48:109-118, 1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (*Plant Molec. Biol.*, 24:25, 1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (*J. Biol. Chem.*, 262:16793, 1987) (nucleotide sequence of rice cysteine proteinase inhibitor), Huub et al., (*Plant Molec. Biol.*, 21:985, 1993) (nucleotide sequence of cDNA encoding tobacco proteinase inhibitor I), and Sumitani et al., (*Biosci. Biotech. Biochem.*, 57:1243, 1993) (nucleotide sequence of *Streptomyces nitrosporeus* α-amylase inhibitor).

An insect-specific hormone or pheromone may also be used. See, for example, the disclosure by Hammock et al., (*Nature*, 344:458, 1990), of baculovirus expression of cloned juvenile hormone esterase, an inactivator of juvenile hormone, Gade and Goldsworthy (Eds. *Physiological System in Insects*, Elsevier Academic Press, Burlington, Mass., 2007), describing allostatins and their potential use in pest control; and Palli et al., (*Vitam. Horm.*, 73:59-100, 2005), disclosing use of ecdysteroid and ecdysteroid receptor in agriculture. The diuretic hormone receptor (DHR) was identified in Price et al., (*Insect Mol. Biol.*, 13:469-480, 2004) as a candidate target of insecticides.

Still other examples include an insect-specific antibody or an immunotoxin derived therefrom and a developmental-arrestive protein. See Taylor et al., (Seventh Int'l Symposium on Molecular Plant-Microbe Interactions, Edinburgh, Scotland, Abstract W97, 1994), who described enzymatic inactivation in transgenic tobacco via production of single-chain antibody fragments.

Nematode resistance has been described, for example, in U.S. Pat. No. 6,228,992 and bacterial disease resistance in U.S. Pat. No. 5,516,671.

K. Modified Fatty Acid, Phytate, and Carbohydrate Metabolism

Genes may be used conferring modified fatty acid metabolism. For example, stearyl-ACP desaturase genes may be used. See Knutzon et al., (*Proc. Natl. Acad. Sci. USA*, 89:2624, 1992). Various fatty acid desaturases have also been described, such as a *Saccharomyces cerevisiae* OLE1 gene encoding Δ9 fatty acid desaturase, an enzyme which forms the monounsaturated palmitoleic (16:1) and oleic (18:1) fatty acids from palmitoyl (16:0) or stearoyl (18:0) CoA (McDonough et al., *J. Biol. Chem.*, 267(9):5931-5936, 1992); a gene encoding a stearoyl-acyl carrier protein delta-9 desaturase from castor (Fox et al., *Proc. Natl. Acad. Sci. USA*, 90(6):2486-2490, 1993); Δ6- and Δ12-desaturases from the cyanobacteria *Synechocystis* responsible for the conversion of linoleic acid (18:2) to gamma-linolenic acid (18:3 gamma) (Reddy et al., *Plant Mol. Biol.*, 22(2):293-300, 1993); a gene from *Arabidopsis thaliana* that encodes an omega-3 desaturase (Arondel et al., *Science*, 258(5086): 1353-1355 1992); plant Δ9-desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al., (*Gene*, 127:87, 1993), for a disclosure of the nucleotide sequence of an *Aspergillus niger* phytase gene. In corn, this, for example, could be accomplished by cloning and then reintroducing DNA associated with the single allele which is responsible for corn mutants characterized by low levels of phytic acid. See Raboy et al., *Plant Physiol.*, 124(1):355-368, 1990.

A number of genes are known that may be used to alter carbohydrate metabolism. For example, plants may be transformed with a gene coding for an enzyme that alters the branching pattern of starch. See Shiroza et al., (*J. Bacteriol.*, 170:810, 1988) (nucleotide sequence of *Streptococcus mutans* fructosyltransferase gene), Steinmetz et al., (*Mol. Gen. Genet.*, 20:220, 1985) (nucleotide sequence of *Bacillus subtilis* levansucrase gene), Pen et al., (*Biotechnology*, 10:292, 1992) (production of transgenic plants that express *Bacillus licheniformis* α-amylase), Elliot et al., (*Plant Molec. Biol.*, 21:515, 1993) (nucleotide sequences of tomato invertase genes), Sergaard et al., (*J. Biol. Chem.*, 268:22480, 1993) (site-directed mutagenesis of barley α-amylase gene), and Fisher et al., (*Plant Physiol.*, 102:1045, 1993) (maize endosperm starch branching enzyme II). The Z10 gene encoding a 10 kD zein storage protein from maize may also be used to alter the quantities of 10 kD zein in the cells relative to other components (Kirihara et al., *Gene*, 71(2): 359-370, 1988).

U.S. Pat. No. 6,930,225 describes maize cellulose synthase genes and methods of use thereof.

L. Resistance to Abiotic Stress

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878 to Thomas et al.

M. Additional Traits

Additional traits can be introduced into a corn variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559 to Fire and Mellow.

Another trait that may find use with the corn variety of the invention is a sequence which allows for site-specific recombination. Examples of such sequences include the FRT sequence, used with the FLP recombinase (Zhu and Sadowski, *J. Biol. Chem.*, 270:23044-23054, 1995); and the LOX sequence, used with CRE recombinase (Sauer, *Mol. Cell. Biol.*, 7:2087-2096, 1987). The recombinase genes can be encoded at any location within the genome of the corn plant, and are active in the hemizygous state.

It may also be desirable to make corn plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews*, 67:16-37, 2003).

In addition to the modification of oil, fatty acid or phytate content described above, it may additionally be beneficial to modify the amounts or levels of other compounds. For example, the amount or composition of antioxidants can be altered. See, for example, U.S. Pat. Nos. 6,787,618 and 7,154,029 and International Patent Appl. Pub. No. WO 00/68393, which disclose the manipulation of antioxidant levels, and International Patent Appl. Pub. No. WO 03/082899, which discloses the manipulation of an antioxidant biosynthetic pathway.

Additionally, seed amino acid content may be manipulated. U.S. Pat. No. 5,850,016 and International Patent Appl. Pub. No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins in which the levels of essential amino acids can be manipulated. International Patent Appl. Pub. No. WO 99/29882 discloses methods for altering amino acid content of proteins. International Patent Appl. Pub. No. WO 98/20133 describes proteins with enhanced levels of essential amino acids. International Patent Appl. Pub. No. WO 98/56935 and U.S. Pat. Nos. 6,346,403, 6,441,274 and 6,664,445 disclose plant amino acid biosynthetic enzymes. International Patent Appl. Pub. No. WO 98/45458 describes synthetic seed proteins having a higher percentage of essential amino acids than wild-type.

U.S. Pat. No. 5,633,436 discloses plants comprising a higher content of sulfur-containing amino acids; U.S. Pat. No. 5,885,801 discloses plants comprising a high threonine content; U.S. Pat. No. 5,885,802 discloses plants comprising a high methionine content; U.S. Pat. No. 5,912,414 discloses plants comprising a high methionine content; U.S. Pat. No. 5,990,389 discloses plants comprising a high lysine content; U.S. Pat. No. 6,459,019 discloses plants comprising an increased lysine and threonine content; International Patent Appl. Pub. No. WO 98/42831 discloses plants comprising a high lysine content; International Patent Appl. Pub. No. WO 96/01905 discloses plants comprising a high threonine content; and International Patent Appl. Pub. No. WO 95/15392 discloses plants comprising a high lysine content.

N. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Barren Plants: Plants that are barren, i.e., lack an ear with grain or have an ear with only a few scattered kernels.

Cg: *Colletotrichum graminicola* rating. Rating times 10 is approximately equal to percent total plant infection.

CLN: Corn Lethal Necrosis (combination of Maize chlorotic mottle virus and Maize dwarf mosaic virus) rating. Numerical ratings are based on a severity scale where 1=most resistant to 9=susceptible.

Cn: *Corynebacterium nebraskense* rating. Rating times 10 is approximately equal to percent total plant infection.

Crossing: The mating of two parent plants.

Cross-pollination: Fertilization by the union of two gametes from different plants.

Cz: *Cercospora zeae-maydis* rating. Rating times 10 is approximately equal to percent total plant infection.

Dgg: *Diatraea grandiosella* girdling rating (values are percent plants girdled and stalk lodged).

Diploid: A cell or organism having two sets of chromosomes.

Dropped Ears: Ears that have fallen from the plant to the ground.

Dsp: *Diabrotica* species root ratings (1=least affected to 9=severe pruning).

Ear-Attitude: The attitude or position of the ear at harvest scored as upright, horizontal, or pendant.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Diameter: The average diameter of the ear at its midpoint.

Ear-Dry Husk Color: The color of the husks at harvest scored as buff, red, or purple.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks, minimum value no less than zero.

Ear-Husk Opening: An evaluation of husk tightness at harvest scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

Early Stand: The percent of plants that emerge from the ground as determined in the early spring.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

ER: Ear rot rating (values approximate percent ear rotted).

$F_1$ Hybrid: The first generation progeny of the cross of two nonisogenic plants.

Final Stand Count: The number of plants just prior to harvest.

GDUs: Growing degree units which are calculated by the Barger Method, where the heat units for a 24-h period are calculated as GDUs=[(Maximum daily temperature+Minimum daily temperature)/2]−50. The highest maximum daily temperature used is 86° F. and the lowest minimum temperature used is 50° F.

GDUs to Shed: The number of growing degree units (GDUs) or heat units required for a variety to have approximately 50% of the plants shedding pollen as measured from time of planting. GDUs to shed is determined by summing the individual GDU daily values from planting date to the date of 50% pollen shed.

GDUs to Silk: The number of growing degree units for a variety to have approximately 50% of the plants with silk emergence as measured from time of planting. GDUs to silk is determined by summing the individual GDU daily values from planting date to the date of 50% silking.

Genetic Complement: An aggregate of nucleotide sequences, the expression of which sequences defines the phenotype in corn plants, or components of plants including cells or tissue.

Genotype: The genetic constitution of a cell or organism.

Haploid: A cell or organism having one set of the two sets of chromosomes in a diploid.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Hm: *Helminthosporium maydis* race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: Chlorotic-lesion type resistance. "+" indicates the presence of Ht chlorotic-lesion type resistance; "−" indicates absence of Ht chlorotic-lesion type resistance; and "+/−" indicates segregation of Ht chlorotic-lesion type resistance. Rating times 10 is approximately equal to percent total plant infection.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow, or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent total plant infection.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination, rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak, or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

Linkage: A phenomenon wherein alleles on the same chromosome tend to segregate together more often than expected by chance if their transmission was independent.

LSS: Late season standability (values times 10 approximate percent plants lodged in disease evaluation plots).

Marker: A readily detectable phenotype, preferably inherited in codominant fashion (both alleles at a locus in a diploid heterozygote are readily detectable), with no environmental variance component, i.e., heritability of 1.

Moisture: The moisture of the grain at harvest.

On1: *Ostrinia nubilalis* 1st brood rating (1=resistant to 9=susceptible).

On2: *Ostrinia nubilalis* 2nd brood rating (1=resistant to 9=susceptible).

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Root Lodging: Root lodging is the percentage of plants that root lodge. A plant is counted as root lodged if a portion of the plant leans from the vertical axis by approximately 30 degrees or more.

Royal Horticultural Society (RHS) Colour Chart Value: The RHS Colour Chart is a standardized reference which allows accurate identification of any color. A color's designation on the chart describes its hue, brightness, and saturation. A color is precisely named by the RHS Colour Chart by identifying the group name, sheet number, and letter, e.g., Yellow-Orange Group 19A or Red Group 41B.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale, where 1 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Self-Pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a corn variety are recovered in addition to the characteristics of the single locus transferred into the variety via the backcrossing technique and/or by genetic transformation.

Sr: *Sphacelotheca reiliana* rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 1 equals best.

STR: Stalk rot rating (values represent severity rating of 1=25% of inoculated internode rotted to 9=entire stalk rotted and collapsed).

Substantially Equivalent: A characteristic that, when compared, does not show a statistically significant difference (e.g., p=0.05) from the mean.

SVC: Southeastern Virus Complex (combination of Maize chlorotic dwarf virus and Maize dwarf mosaic virus) rating; numerical ratings are based on a severity scale where 1=most resistant to 9=susceptible.

Tassel-Anther Color: The color of the anthers at 50% pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50% shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: Weight of the grain in pounds for a given volume (bushel) adjusted to 15.5% moisture.

Tissue Culture: A composition comprising isolated cells of the same or a different type or a collection of such cells organized into parts of a plant.

Transgene: A genetic locus comprising a sequence which has been introduced into the genome of a corn plant by transformation or site-specific recombination.

Yield: Yield of grain at harvest adjusted to 15.5% moisture.

O. Deposit Information

A deposit of corn hybrid SVSK6143 and inbred parent lines SHY-6S15-9078LP and SHY-6RHBE322, disclosed above and recited in the claims, has been made with the American Type Culture Collection (ATCC), 10801 University Blvd., Manassas, Va. 20110-2209. The dates of deposit for hybrid SVSK6143 and inbred parent lines SHY-6S15-9078LP and SHY-6RHBE322 were Apr. 21, 2017, May 22, 2017, and May 22, 2017, respectively. The accession numbers for those deposited seeds of corn hybrid SVSK6143 and inbred parent lines SHY-6S15-9078LP and SHY-6RHBE322 are ATCC Accession No. PTA-124111, ATCC Accession No. PTA-124211, and ATCC Accession No. PTA-124212, respectively. Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed:

1. A corn plant comprising at least a first set of the chromosomes of corn line SHY-6S15-9078LP or corn line SHY-6RHBE322, a sample of seed of said lines having been deposited under ATCC Accession Number PTA-124211 and ATCC Accession Number PTA-124212, respectively.

2. A corn seed that produces the plant of claim 1.

3. The plant of claim 1, wherein the plant is a plant of corn hybrid SVSK6143, a sample of seed of said hybrid having been deposited under ATCC Accession Number PTA-124111.

4. The seed of claim 2, wherein the seed is a seed of corn hybrid SVSK6143, a sample of seed of said hybrid having been deposited under ATCC Accession Number PTA-124111.

5. The seed of claim 2, wherein the seed is a seed of corn line SHY-6S15-9078LP or corn line SHY-6RHBE322.

6. A plant part of the plant of claim 1, wherein the plant part comprises a cell of said plant.

7. A corn plant having all the physiological and morphological characteristics of the corn plant of claim 1.

8. A tissue culture of regenerable cells of the plant of claim 1.

9. A method of vegetatively propagating the corn plant of claim 1, the method comprising the steps of:
    (a) collecting tissue capable of being propagated from the plant according to claim 1; and
    (b) propagating a corn plant from said tissue, wherein said propagated corn plant comprises all of the morphological and physiological characteristics of the corn plant of claim 1.

10. A method of introducing a trait into a corn line, the method comprising:
    (a) utilizing as a recurrent parent a plant of corn line SHY-6S15-9078LP or corn line SHY-6RHBE322, by crossing a plant of corn line SHY-6S15-9078LP or corn line SHY-6RHBE322 with a donor corn plant that comprises a trait to produce F progeny, a sample of seed of said lines having been deposited under ATCC Accession Number PTA-124211 and ATCC Accession Number PTA-124212, respectively;
    (b) selecting an $F_1$ progeny that comprises the trait;
    (c) backcrossing the selected $F_1$ progeny with a plant of the same corn line used as the recurrent parent in step (a) to produce backcross progeny;
    (d) selecting a backcross progeny comprising the trait and the morphological and physiological characteristics of the recurrent parent corn line used in step (a); and
    (e) repeating steps (c) and (d) three or more times to produce a selected fourth or higher backcross progeny.

11. A corn plant produced by the method of claim 10, wherein said plant comprises said introduced trait and otherwise comprises all of the morphological and physiological characteristics of the plant obtained from said deposited seed when grown under the same environmental conditions.

12. A method of producing a corn plant comprising an added trait, the method comprising introducing a transgene conferring the trait into a plant of corn hybrid SVSK6143, corn line SHY-6S15-9078LP, or corn line SHY-6RHBE322, a sample of seed of said hybrid and lines having been deposited under ATCC Accession Number PTA-124111, ATCC Accession Number PTA-124211, and ATCC Accession Number PTA-124212, respectively.

13. A corn plant produced by the method of claim 12, wherein said plant comprises said added trait and otherwise comprises all of the morphological and physiological characteristics of the plant obtained from said deposited seed when grown under the same environmental conditions.

14. A corn plant comprising at least a first set of the chromosomes of corn line SHY-6S15-9078LP or corn line SHY-6RHBE322, a sample of seed of said lines having been deposited under ATCC Accession Number PTA-124211 and ATCC Accession Number PTA-124212, further comprising a transgene.

15. The plant of claim 14, wherein the transgene confers a trait selected from the group consisting of male sterility, herbicide tolerance, insect resistance, pest resistance, disease resistance, modified fatty acid metabolism, environmental stress tolerance, modified carbohydrate metabolism, and modified protein metabolism.

16. A corn plant comprising at least a first set of the chromosomes of corn line SHY-6S15-9078LP or corn line SHY-6RHBE322, a sample of seed of said lines having been deposited under ATCC Accession Number PTA-124211 and ATCC Accession Number PTA-124212, further comprising a single locus conversion and otherwise comprising all of the morphological and physiological characteristics of the plant obtained from said deposited seed when grown under the same environmental conditions.

17. The plant of claim 16, wherein the single locus conversion confers a trait selected from the group consisting of male sterility, herbicide tolerance, insect resistance, pest resistance, disease resistance, modified fatty acid metabolism, environmental stress tolerance, modified carbohydrate metabolism, and modified protein metabolism.

18. A method for producing a seed of a corn plant derived from at least one of corn hybrid SVSK6143, corn line SHY-6S15-9078LP, or corn line SHY-6RHBE322, the method comprising the steps of:
(a) crossing a corn plant according to claim 1 with itself or a second corn plant; and
(b) allowing seed of a hybrid SVSK6143, line SHY-6S15-9078LP, or line SHY-6RHBE322-derived corn plant to form.

19. A method of producing a seed of a hybrid SVSK6143, line SHY-6S15-9078LP, or line SHY-6RHBE322-derived corn plant, the method comprising the steps of:
(a) producing a hybrid SVSK6143, line SHY-6S15-9078LP, or line SHY-6RHBE322-derived corn plant from a seed produced by crossing a corn plant according to claim 1 with itself or a second corn plant; and
(b) crossing the hybrid SVSK6143, line SHY-6S15-9078LP, or line SHY-6RHBE322-derived corn plant with itself or a different corn plant to obtain a seed of a further hybrid SVSK6143, line SHY-6S15-9078LP, or line SHY-6RHBE322-derived corn plant.

20. The method of claim 19, the method further comprising repeating said producing and crossing steps of (a) and (b) using a seed from said step (b) for producing a plant according to step (a) for at least one generation to produce a seed of an additional hybrid SVSK6143, line SHY-6S15-9078LP, or line SHY-6RHBE322-derived corn plant.

21. A method of producing an ear of corn, the method comprising:
(a) obtaining the plant according to claim 1, wherein the plant has been cultivated to maturity; and
(b) collecting an ear of corn from the plant.

22. The plant of claim 1, wherein the plant is a plant of said corn line SHY-6S15-9078LP or corn line SHY-6RHBE322.

* * * * *